United States Patent [19]

Wieser

[11] 4,371,816
[45] Feb. 1, 1983

[54] CONTROL CIRCUIT FOR AN ULTRASONIC DENTAL SCALER

[76] Inventor: Alfred Wieser, Usingerstrasse 33, 6391 Usingen 2, Fed. Rep. of Germany

[21] Appl. No.: 754,886

[22] Filed: Dec. 27, 1976

[30] Foreign Application Priority Data

Dec. 30, 1975 [DE] Fed. Rep. of Germany ....... 2559198
Jan. 12, 1976 [DE] Fed. Rep. of Germany ....... 2600877

[51] Int. Cl.³ ............................................. H01V 9/00
[52] U.S. Cl. ............................................. 318/116
[58] Field of Search ................ 310/316, 318, 26, 317; 318/116, 118, 119

[56] References Cited

U.S. PATENT DOCUMENTS

| | | | |
|---|---|---|---|
| 2,799,787 | 7/1957 | Güttner et al. | 310/317 X |
| 2,917,691 | 12/1959 | DePrisco et al. | 318/118 |
| 3,443,130 | 5/1969 | Shoh | 310/316 |
| 3,447,051 | 5/1969 | Attwood et al. | 318/118 X |
| 3,489,930 | 1/1970 | Shoh | 318/118 |
| 3,526,792 | 9/1970 | Shoh | 310/316 |
| 3,544,866 | 12/1970 | McLeroy | 318/118 |
| 3,573,781 | 4/1971 | Shoh | 310/317 X |
| 3,586,936 | 6/1971 | McLeroy | 318/118 |
| 3,668,486 | 6/1972 | Silver | 318/116 X |
| 3,727,112 | 4/1973 | Popescu | 310/316 X |
| 3,743,868 | 7/1973 | Kawada | 310/118 X |
| 3,819,961 | 6/1974 | Bourgeois et al. | 310/316 |
| 4,056,761 | 11/1977 | Jacoby et al. | 318/118 X |

Primary Examiner—Donovan F. Duggan
Attorney, Agent, or Firm—Litman, Day & McMahon

[57] ABSTRACT

A control circuit for an ultrasonic dental scaler, comprising a transducer driven by a frequency-controlled oscillator, is disclosed. The control circuit is operable for continuously regulating the oscillator frequency at substantially the same value as the resonant frequency of the transducer with a dental tool attached to it and for controlling the mechanical power output of the transducer. The transducer can be drivingly connected to a work tool for transmitting mechanical energy thereto. The regulation of the oscillator frequency is accomplished by simultaneously applied control signals derived from the current passing through the transducer and from the voltage across the transducer, to compensate for supply voltage variations. Moreover, the mechanical power output of the transducer is controlled such that it is reduced whenever the contact pressure of the work tool exceeds a predetermined maximum value. Such excessive pressure is monitored as the amplitude or phase variation of the voltage or of the current of the transducer.

6 Claims, 11 Drawing Figures

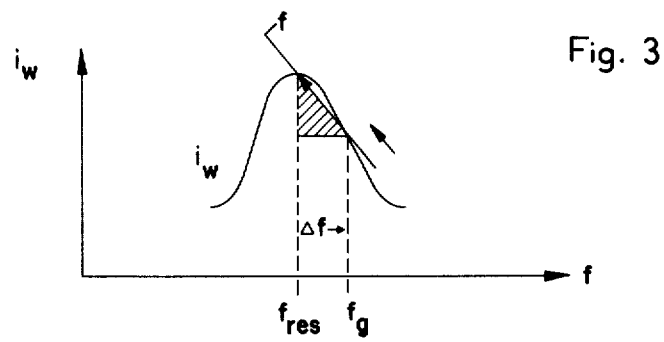
Fig. 3
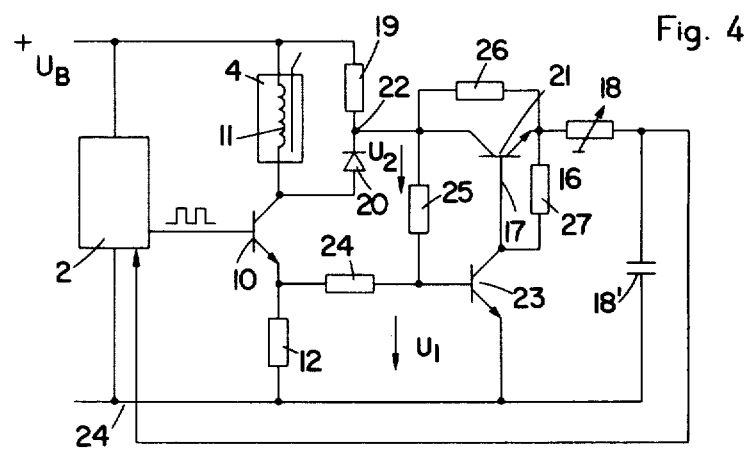
Fig. 4
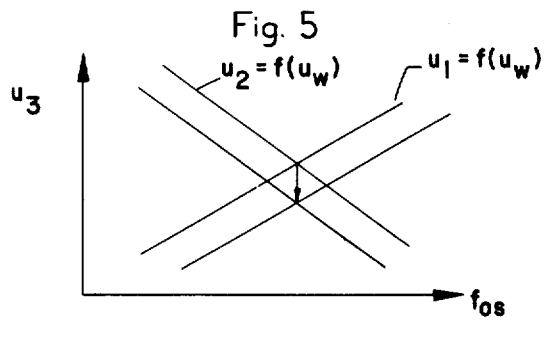
Fig. 5
Fig. 6

CONTROL CIRCUIT FOR AN ULTRASONIC DENTAL SCALER

BACKGROUND OF THE INVENTION

1. Field of the Invention

The present invention relates generally to ultrasonic dental scalers and more particularly to control circuits for driving the same.

2. Description of the Prior Art

Ultrasonic treatment devices, especially for the removal of tartar from teeth, etc., by means of a magnetostrictive transducer, and a tool selected from a number of such tools secured to it, are generally known.

The common feature of these instruments is that the magnetostrictive transducer, together with the selected, inserted tool or the tool tip, represents a mechanical vibratory system which must be driven at resonant frequency, in order to ensure optimum power output. Many conditions, such as the differences in the length of the tools or of the tool inserts, their wear, the changes in the vibratory system, as well as the mechanical load applied to the tool under operating conditions effect a frequency shift of the vibratory system. Such frequency shifts must be compensated for, either manually by changing the frequency of the ultrasonic generator, or, alternatively, by automatic frequency correction adjustment.

In the known driving and control arrangements which are provided with automatic frequency correction adjustments, either self-excited generators or oscillators are continually frequency-adjusted by means of a feedback signal generated in a coil which is operatively associated with the transducer. Alternatively, additional sensor elements, for example piezoelectric elements, have been provided in the transducer, which supply a signal for the correction adjustment of the oscillator.

Moreover, since dental treatment devices of this kind are driven with high power, the possibility exists that, on careless handling of the device, damage is done to a tooth due to excessive pressure exerted by the tool on the tooth. This danger exists especially in the case of dental treatment devices having automatic frequency adjustment, i.e. tuning means, for the oscillator driving the transducer, because in these devices the transducer continuously operates at a frequency which ensures maximum power output of the transducer.

SUMMARY OF THE INVENTION

The purpose of the present invention is to overcome the disadvantages of generally known driving and control arrangements and to provide an automatic driving and control circuit, which automatically compensates for fluctuations in supply line voltage, which is operable over a wide correction adjustment range, which is simple and cheap to produce, is accommodated within the smallest possible space and which especially reduces the production and replacement costs of the transducer, as well as of the tool inserts.

Moreover, the control arrangement for driving the transducer is designed so that when a specific, predetermined or adjustable contact pressure between the tool and a tooth is exceeded, the power to the transducer is switched off, or at least reduced.

In its broadest aspects, the present invention relates to a control circuit for an ultrasonic dental scaler designed to continuously readjust the oscillator frequency to be maintained at the same value as the natural frequency of the vibratory system, such readjustment being accomplished by means of a first control signal derived from the current passing through the transducer and a second, simultaneous, control signal which is derived from the voltage across the transducer. This control criterion is also utilized in sensing the contact pressure of the work tool in order to switch off or reduce the power output of the transducer.

The invention is based on the recognition that a magnetostrictive transducer has characteristics whose current and voltage on approaching the resonant frequency of the transducer will substantially increase and have their real maximum values at or near the resonant frequency. This fact is used as the control criterion for the correction adjustment of the invention in which the correction adjustment characteristics of the oscillator, i.e. the frequency variation of the oscillator must have a suitable variation form in relation to the regulating voltage supply to the oscillator, because a frequency deviation can be compensated only if, by means of an opposite regulating magnitude the original condition, with respect to current and voltage, is once again restored. This can occur in the present case only if, in addition to the correct starting transition frequency behavior, the direction of the correction adjustment is also specified. This means that that part of the resonance curve of the transducer which is used for the detuning and correction adjustment in relation to a predetermined basic frequency is determined. The frequency supplied by the oscillator at the moment of switching on is designated as the basic frequency. Its tendency is determined by the starting transient frequency behavior of the circuit and its level is suitably established above the resonant frequency of the transistor in the inductive region of the resonance curve of the transducer. It is, however, also possible to select the basic frequency lower than the resonant frequency of the transducer.

The driving and control circuit according to the invention has especially the advantage that by means of the simultaneous application of the first control signal derived from the current flowing through the transducer and the second control signal derived from the voltage across the transducer for the purpose of generating regulating voltage for correction adjustment of the oscillator, it is ensured that the frequency-correction adjustment is independent from changes in supply voltage over wide limits.

The control criterion used for the control of contact pressure of the tool by switching off the transducer or by reduction of the power output of the transducer is preferably the voltage or current-frequency characteristic and/or the frequency-dependent phase variation of the voltage or of the current of the transducer which has oscillating circuit characteristics.

The dental treatment device according to the invention or its safety circuit, which causes the switching off of the transducer or the reduction of the power output of the transducer, can be realized without special additional expenditure.

The features of the present invention, which are believed to be novel, are set forth with particularity in the appended Claims. The present invention, both as to its organization and manner of operation, together with the further advantages thereof, may best be understood by reference to the following description taken in connection with the accompanying drawings.

BRIEF DESCRIPTION OF THE DRAWINGS

FIG. 3 is a current-frequency diagram of the transducer of the circuit of FIGS. 1 and 2;

FIG. 4 is a modified embodiment of a driving and control circuit according to the present invention;

FIG. 5 is a diagrammatic representation of the influence of the first and second control signals on the regulating voltage supplied to the oscillator, plotted as a function of oscillator frequency;

FIG. 6 is a diagrammatic representation showing the dependence of the oscillator frequency on the regulating voltage supplied to the oscillator;

DETAILED DESCRIPTION OF THE PREFERRED EMBODIMENTS

Figure 1:
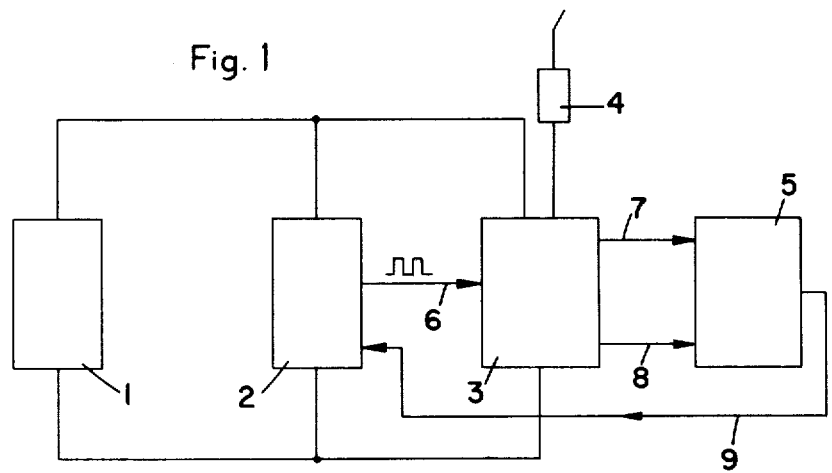
FIG. 1 is a block diagram of a driving and control circuit according to the present invention.

The circuit diagram of a basic embodiment shown in FIG. 1 includes a direct voltage supply source 1 and an oscillator 2, whose frequency can be correction-adjusted by a direct voltage, which oscillator can be, for example, a multivibrator of conventional design. The circuit also has a power output stage 3 for the electromechanical transducer 4, located in the handpiece of the ultrasonic treatment device. The circuit also includes a network 5 for combining signals generated in the stage 3, as explained below.

The output signal of the oscillator 2 is fed via a conductor 6 to the power output stage 3 and there it is amplified for driving the transducer 4. The output stage 3 is connected by conductors 7 and 8 with the network 5. A first control signal, derived from the transducer current, is supplied via conductor 8 to the network 5, and a second control signal, derived from the voltage of the transducer, is supplied via conductor 7. In the network 5, a regulating voltage is generated from both control signals, which is fed back from the output of network 5 via a conductor 9 to the oscillator 2, for regulating the frequency of the oscillator, in order to continually re-adjust, whenever necessary, the oscillator frequency to maintain it at a value which substantially equals the instantaneous mechanical resonant frequency of the vibratory system formed by the transducer 4 and a selected dental tool connected to it. The regulation within the region of the resonant frequency of the transducer 4 also functions in the case of changes of the frequency-determining parameters or in the case of changes in the supply source voltage.

Figure 2:
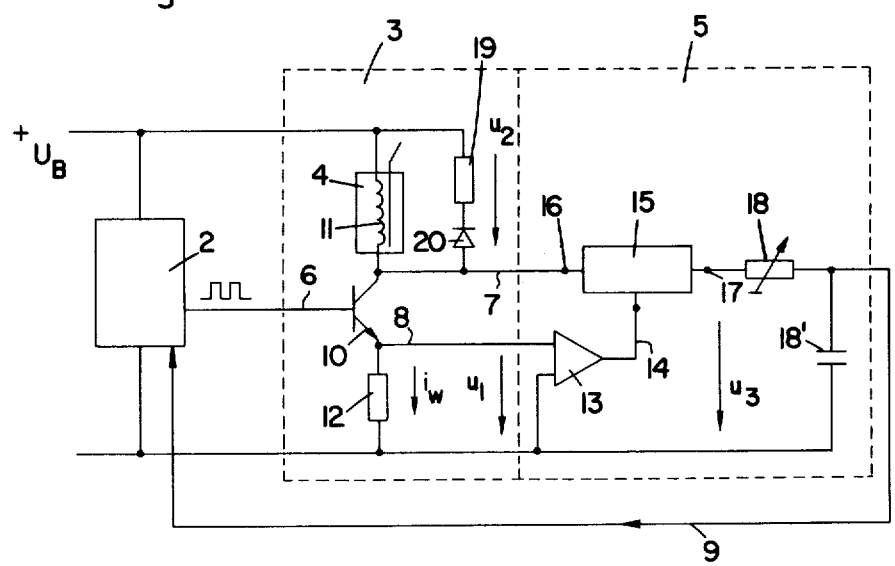
FIG. 2 is a block diagram of the control circuit of FIG. 1, illustrated in greater detail.

FIG. 2 illustrates in detail an embodiment of the driving and control circuit of FIG. 1. The circuit shown in FIG. 2 has the oscillator 2 of conventional design and of the type of which the frequency can be adjusted by a direct control voltage. The output signal of the oscillator 2 is fed through conductor 6 to the base of a transistor 10 of the power output stage 3, into whose collector current circuit a coil 11 of the transducer 4 is connected as the load. A resistor 12 is provided in the emitter current circuit for deriving a first control signal $U1 = -f(i_w)$, which is a function of the current passing through coil 11 of the transducer 4. This first control signal U1 is applied to the input of an operational amplifier 13, whose output signal, over the conductor 14, constitutes the control input to a feedback signal generator 15. The generator 15 is basically an adjustable resistive component with one input terminal 16, one output terminal 17, and a control input 14. In its simplest form, it may be a variable active component, for example a transistor.

The input terminal 16 of the feedback signal generator 15 receives a second control signal $U2 = f(u_w)$ derived from the voltage on the transducer 4, actually on the coil 11 of a magnetostrictive driving element of the transducer. This results in a regulating voltage U3, appearing on the output terminal 17 of the feedback signal generator 15. The amplitude or magnitude of this second control signal U2 is therefore influenced at the same time by the first, which is the control signal U1.

The regulating voltage U3 is fed back via an adjustable resistor 18 and via the conductor 9 to the oscillator 2 for regulating the oscillator frequency. The resistor 18, together with a capacitor 18', forms a low pass filter arrangement, which ensures the correct starting frequency of the regulating circuit. The low pass filter arrangement, consisting of the resistor 18 and of the capacitor 18', can, however, be used at the same time as the frequency-determining element for the oscillator, i.e. multivibrator 2.

In the collector current circuit of the transistor 10 there is also provided a series circuit consisting of a damping resistor 19 and a diode 20. These elements are connected in parallel to the coil 11 of the transducer 4. This series circuit consisting of the damping resistor 19 and diode 20 is used to ensure that, on blocking of the transistor 10, an overshoot of the voltage on the collector of this transistor or at the end of the coil 11 is avoided.

FIG. 3 shows the variation of the current $i_w$ flowing through the transducer 4, actually through its coil 11, as a function of frequency. As seen, this current $i_w$ has its maximum at the resonant frequency $f_{res}$, while the current is of lesser magnitude at higher and lower frequencies. This current-frequency characteristic of the transducer 4 is used as a discriminator characteristic curve. Suitably, the basic frequency $f_g$ of the oscillator 2 is higher than any possible, or expected, resonant frequency within the range of resonant frequencies of the transducer 4. The specific frequency, at which the oscillator 2 operates in the absence of the regulating voltage U3 or in the case of the open regulating circuit, is designated the basic frequency $f_g$. Since the resonant frequency of the transducer 4 is determined by the geometrical form, as well as especially by the mass, of the specific, selected tool connected with the transducer 4 (the resonant frequency of the transducer 4 is reduced progressively with increasing weight and shape of the tool secured to the transducer), it is therefore convenient to select the basic frequency $f_g$ for the oscillator 2 so that, in all cases, it will be higher than, or, alternatively, equal to the resonant frequency of the transducer 4 in the absence of a tool.

The oscillator 2 has the correction adjustment characteristic shown in FIG. 6, i.e. the oscillator frequency $f_{os}$ increases together with the increasing amplitude of the regulating voltage U3, while the operational amplifier 13, as well as the feedback signal generator are dimensioned or designed in such a manner that an increase of the amplitude of the control signal U1, in the case of the constant control signal U2, leads to a decrease of the amplitude of the regulating voltage U3 and vice versa.

Upon switching on of the supply voltage source 1, the oscillator 2 applies a signal at the basic frequency $f_g$ to the base of the transistor 10. This causes a pulsating current to flow through the coil 11 and hence also generates the control signal U1, whose amplitude is proportional to this current. By means of the operational amplifier 13, the control voltage U1 causes an increase of the resistance of the feedback signal generator 15 and hence a reduction of the magnitude of the regulating voltage U3 appearing at the output 17 of the generator 15. According to FIG. 6, a reduction of the magnitude of the regulating voltage U3 leads to a reduction of the oscillator frequency $f_{os}$ which has the result that, according to FIG. 3, the current through the coil 11 of the transducer 4, as well as through the resistor 12, will increase and hence the magnitude of the control signal U1 will also increase. This increase of the magnitude of the control signal U1 results in further increase of the resistance of the feedback signal generator 15 and hence further reduction of the magnitude of the regulating voltage U3 occurs. This also results in further reduction of the oscillator frequency $f_{os}$. This effect is cumulative, because each reduction of the oscillator frequency $f_{os}$ causes an increase of the current through the transducer 4, and thus an increase of the amplitude of the control signal U1. The latter results, once again, by means of the feedback signal generator 15, in a reduction of the magnitude of the regulating voltage U3. This tuning, i.e. frequency regulating process is terminated when the resonant frequency $f_{res}$ of the transducer 4 has been reached, because on a further reduction of the frequency beyond this resonance point the current passing through the transducer is reduced once again (see FIG. 3). The correction, i.e. adjustment range, is hence the region illustrated in FIG. 3 by the area shown with cross hatching. In this region, the oscillator 2 is automatically frequency-adjusted such that it is brought into resonance with the natural frequency of the transducer 4, together with any selected tool inserted. Since the magnitude of the regulating voltage U3 depends also upon the control signal U2, i.e. upon the voltage at the collector of the transistor 10, it is hence ensured that the fluctuations of the supply voltage, which occur under normal operating conditions, cannot interfere with the above-described tuning process, i.e. frequency readjustment.

When the circuit has been adjusted to the resonant frequency $f_{res}$ of the transducer 4, as a result of the above-described correction adjustment, and when the supply voltage is reduced, this decrease will lead to a reduction of the current flowing through the coil 11, as well as through the resistor 12. Hence, it will also lead to a reduction of the magnitude of the control signal U1. According to the above consideration, however, such reduction of the magnitude of the control signal U1 would result in an amplification of the magnitude of the regulating voltage U3, which then causes a mistuning of the oscillator 2. This mistuning of the oscillator 2, which is caused only by the lowering of the supply voltage, is avoided by the circuit of the invention, because the current flowing through the coil 11 is reduced and the positive reaction voltage, which appears on switching off of the transistor 10 on the collector of this transistor or on the damping resistor 19, is also simultaneously reduced. As a result, the amplification of the regulating voltage U3, caused by the reduction of the control signal U1, resulting from a reduction of the magnitude of the control signal U2, is once again compensated. The regulating voltage U3 is hence independent of fluctuations of the supply voltage which are known to occur frequently and then could disturb normal operating conditions.

An especially useful embodiment of the driving and control circuit, according to the invention, is shown in FIG. 4. This circuit is identical with the circuit shown in FIG. 2, as far as the oscillator 2, as well as the power output stage formed by the transistor 10 for the actuation and control of the coil 11 of the transducer 4 are concerned.

A transistor 21 is provided to constitute the feedback signal generator in the embodiment shown in FIG. 4 and the control signal U2 is fed to its collector. This control signal is derived not from the collector of the transistor 10, but at the point 22, i.e. the junction between the damping resistor 19 and the diode 20. The transistor 21, which is used as a variable resistor, is connected with its collector-emitter circuit between this junction 22 and the low pass filter arrangement consisting of the resistor 18 and the capacitor 18'. The base of the transistor 21 is connected to the collector of a transistor 23, whose base-emitter circuit is connected in series with a resistor 24 to which the resistor 12 is connected in parallel, this part of the circuit corresponding to those components of the circuit of FIG. 2 which generate the control signal U1. Thus, transistor 23 is seen to correspond to amplifier 13.

The resistors 25, 26 and 27 are used for adjusting the operating point of the transistors 21 and 23. The resistor 25 connects the base of the transistor 23 with the point 22. The resistor 26 connects the collector with the emitter of the transistor 21, and the resistor 27 connects the emitter of transistor 21 with the collector of the transistor 23.

As far as the frequency correction, i.e. regulation of the frequency for the purpose of tuning is concerned, the circuit according to FIG. 4 operates as the circuit according to FIG. 2. Thus, in the circuit shown in FIG. 4, the oscillator 2 is adjusted in such a manner that its basic frequency $f_g$ is at a value above any expected resonant frequency $f_{res}$ of the vibratory system, including transducer 4. Therefore, after switching on the supply voltage, the frequency of oscillator 2 is adjusted until it is substantially identical with the resonant frequency $f_{res}$. During this time, the magnitude of the control signal U1 increases steadily. This is so because an increase of the magnitude of the control voltage U2 has the result that the collector-emitter circuit of the transistor 21, controlled by the transistor 23, will have higher ohmic resistance, so that the magnitude of the regulating voltage U3, appearing at the emitter of the transistor 21, will be reduced. A reduction of the regulating voltage U3 leads, according to FIG. 6, to a further reduction of the oscillator frequency. This leads once again to an increase of the current flowing through the resistor 12 and hence to an increase of the amplitude of the control signal U1, etc., until the resonant frequency $f_{res}$ has been reached.

The circuit according to FIG. 4, however, has the special advantage of facilitating the regulation of the output power of the transducer 4 by the supply voltage or by changes in the amplitude of the supply voltage. The important feature in the embodiment shown in FIG. 4 is that the control signal U2 is collected at junction 22 between the damping resistor 19 and the diode 20 (when using npn transistors at the cathode of the diode 20). The voltage components appearing at the junction 22, consisting exclusively of the positive portions of the feedback voltage on the damping resistor 15 and of the supply voltage, exhibit an especially advantageous regulating behavior for the fluctuations of the supply voltage.

If, for example, the supply voltage used for the regulation of the output power of the transducer 4 is reduced, then this leads to a reduction of the current flowing through the coil 11 of the transducer 4 as well as through the resistor 12. The reduction of the amplitude, i.e. magnitude of the control signal U1 resulting from this would lead, of necessity, to an increase of the amplitude of the regulating voltage U3 and hence to an undesirable mistuning of the oscillator 2. Since the magnetic energy stored in coil 11 is also reduced at the same time and hence also the amplitude of the positive reaction voltage on the damping resistor 19 is reduced, the frequency correction adjustment of the oscillator 2 is not influenced by changes in supply voltage. This is so because the control signals U1 and U2 are changed in the same direction, and the control signals U1 and U2 have an opposite effect on the frequency of the oscillator 2, as can be seen from FIG. 5. While a reduction of the control signal U1 leads to an increase of the frequency $f_{os}$ of the oscillator, a reduction of the control signal U2 results in a reduction of the frequency $f_{os}$ of the oscillator 2. A change in the supply voltage will hence lead only to a change of the power output of the transducer 4.

Figure 7:
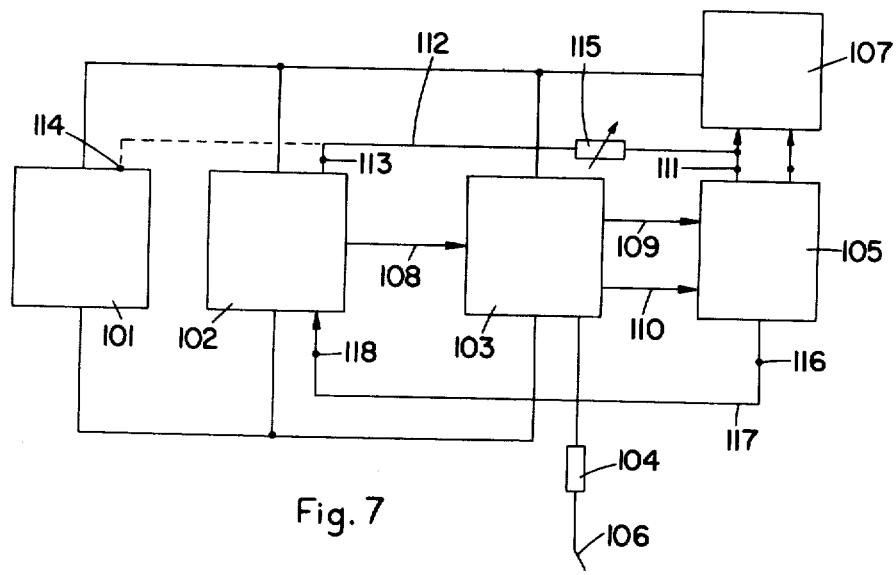
FIG. 7 is a block diagram of a driving and control circuit utilizing a safety circuit which reduces the mechanical power output in case of excessive contact pressure.

The embodiment of a control circuit for an ultrasonic dental instrument of the type referred to as a scaler, shown in FIG. 7, consists basically of a direct current supply source 101, an oscillator 102 whose frequency can be adjusted by direct voltage, which oscillator is, for example, a multivibrator of conventional design, and an actuating or power output stage 103 for an electromagnetic transducer 104 which is accommodated within a handle of the dental instrument. A triggering circuit 105 is also provided, which, when a specific, preferably adjustable, maximum contact pressure of a tool 106 held on the transducer is exceeded, causes the switching off, or at least a reduction of the power output of the transducer 104. In addition, an arrangement 107 is provided which is used to indicate the adjusted maximum power or the maximum contact pressure of the tool 106.

The output signal of the oscillator 102 is supplied via a conductor 108 to the output stage 103 and is amplified for driving the transducer 104. The stage 103 is connected by conductors 109 and 110 to the triggering device 105 which supplies on its output 111 a signal which depends on the load applied to the transducer 104, and is thus a function of the contact pressure of the tool 106. This signal is supplied via a conductor 112 to an input 113 of the oscillator 102. In the case of contact pressure exceeding the adjusted, or preselected, maximum contact pressure of the tool 106, the frequency of the oscillator 102 is adjusted in such a manner that it will be outside the resonant frequency of the transducer 104. As a result, the output of the transducer 104 is reduced or is at least of such low level that it is not able to produce mechanical power at all.

It is also possible that the signal supplied via the conductor 112 to the input 113 of the oscillator 102 can be used for the control of the duty cycle of a multivibrator used as an oscillator. This is done to control the power output of the transducer 104 in relation to the contact pressure of the tool 106. Alternatively, the signal on the output 111 of the triggering circuit 105 can also be used, when a maximum contact pressure on the tool 106 is exceeded, to reduce the voltage of the supply source 101 and hence to reduce the output power of the transducer 104. The direct voltage supply source 101 is provided for this purpose with a control input 114, to which the signal on the output 111 of the triggering circuit 105 is supplied, as shown in FIG. 7 with broken lines. For the adjustment of maximum contact pressure of the tool 106, a regulator 115, suitably an adjustable resistor, as shown, is used, which is connected into the conductor 112.

In the circuit shown in FIG. 7, the voltage across, and the current through the transducer 104 are used for controlling the frequency of the oscillator, as described in connection with the circuit as shown in FIG. 2, and, moreover, one or the other is used as a criterion or measured value for the actual contact pressure of the tool 106. In this aspect, the invention is based on the recognition that an electromechanical transducer, especially a magnetostrictive or piezoelectric transducer, has an oscillating circuit characteristic (for example, phase-equalizing characteristic). For example, the current flowing through the transducer 104 reaches a maximum value when the transducer is actuated by a signal whose frequency corresponds to the natural frequency of the vibratory system of which the transducer 104 forms part. This natural frequency of the system is influenced by the geometrical shape of the tool 106 and by the mass of this tool, as well as by the contacting pressure with which the tool is pressed against the tooth of a patient. Hence, for example, in the case of high contacting pressure, the resonant frequency of the oscillating, i.e. vibratory system formed by the transducer 104 and the tool 106 is lower than in the case of low contacting pressure. The change of the amplitude and/or of the phase of the current or of the voltage at the transducer due to the shift of the resonant frequency is used as the measured value or as the criterion for the actual contact pressure of the tool 106 and it is analyzed in the triggering circuit 105 for generating the signal in the conductor 112.

The automatic correction of the frequency of the oscillator 102 in the circuit for dental treatment devices called scalers, shown in FIG. 7, is provided in such a manner that the oscillator 102 produces an output whose frequency corresponds to the instantaneous, resonant frequency of the transducer 104. For this purpose, the triggering circuit 105 generates simultaneously a regulating voltage which is supplied from the output terminal 116 of the triggering circuit 105, via the conductor 117, to the input terminal 118 of the oscillator 102 for its correction regulation. As described hereinbelow, it is also possible to feed back a single signal from the triggering circuit 105 to the oscillator 102, which, when operating below the specific or adjusted maximum permissible contact pressure of the tool 106, causes a correction adjustment of the oscillator 102 and when the maximum permissible contact pressure is exceeded, the oscillator 102 is misadjusted away from the resonant frequency of the transducer 104 to such an extent that the transducer 104 can no longer product mechanical power.

Figure 8:
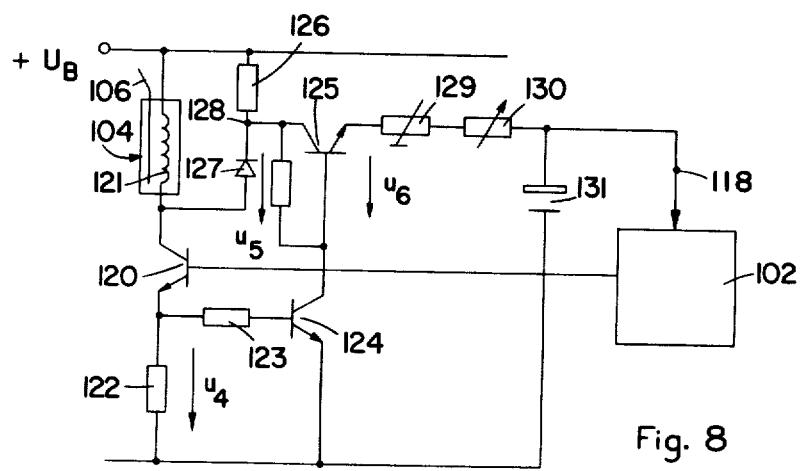
FIG. 8 is a block diagram of the circuit of FIG. 7, illustrated in greater detail.

FIG. 8 shows in greater detail an embodiment of the circuit shown in general in FIG. 7. The circuit includes the oscillator 102 whose frequency can be adjusted by a direct voltage. The oscillator 102 is formed by a conventional multivibrator and its output signal is fed to the base of a transistor 120, in whose collector circuit the coil 121 of the transducer 104 is connected as the load. A resistor 122, which produces a first control signal $U4 = f(i_w)$ depending on the current passing through the transducer 104, actually through the coil 121, is connected in the emitter circuit. This first control signal U4 is supplied via a resistor 123 to the base of a transistor 124, whose collector is connected to the base of a transistor 125 which acts as a variable resistor. Transistors 124 and 125 can be seen to correspond to transistors 23 and 21 of FIG. 4, respectively.

The coil 121 of the transducer 104 is connected in parallel to a series-connected circuit branch consisting of a damping resistor 126 and a diode 127. This series circuit or the damping resistor 126 is used for damping the overshoot of the voltage on the collector of this transistor or at the end of the coil which is connected to the collector of transistor 120. On blocking of the transistor 120, the magnetic energy stored in the coil 121 is dissipated in the damping resistor 126. By means of the current flowing through the diode 127 and the resistor 126, voltage pulses which are superposed on the supply voltage $U_B$ are generated at the junction 128 between the diode 127 and the resistor 126, on blocking of the transistor 120. The voltage at the junction 128, which depends on the voltage across the coil 121 of the transducer 104 is supplied as a second control signal $U5 = -s(U_w)$ to the collector of the transistor 125, so that a regulating voltage U6 is generated at the emitter of the transistor 125. The amplitude of the voltage U6 is supplied to the oscillator 102 for the correction regulation of frequency via a trimmer 129 as well as via an adjustable resistor 130, which, together with a capacitor 131, form a low pass filter.

This frequency correction regulation, i.e. the automatic continuous adjustment of the oscillator 102 to the instantaneous resonant frequency of the vibratory system of transducer 104 is carried out in this case in the following manner. Upon switching on the supply voltage $U_B$, i.e. the direct voltage supply source 101, the oscillator 102 supplies to the base of the transistor 120 a control signal at the basic frequency $f_g$ which is suitably higher than any possible resonant frequency $f_{res}$ of the vibratory system with transducer 104. In this case, that frequency at which the oscillator 102 operates in the absence of the regulating voltage U6 or in the case of the open regulating circuit and which is established only by the frequency-determining elements of the oscillator 102 is designated the basic frequency $f_g$. Since the resonant frequency of the transducer vibratory system is determined by the geometrical shape as well as the mass of the tool 106 connected to the transducer 104 and this resonant frequency decreases together with an increasing mass of the tool held on the transducer, it is therefore useful to select the basic frequency $f_g$ for the oscillator 102 so that it is higher, or at least equal to the resonant frequency of the transducer 104 without a tool 106.

Figure 9:
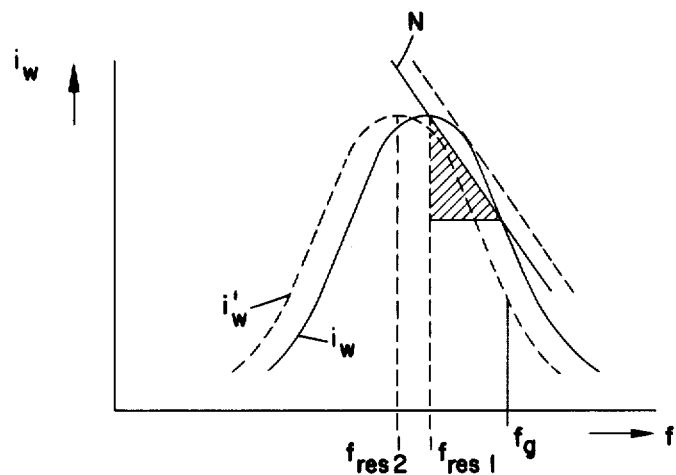
FIG. 9 is a current-frequency diagram showing the characteristic of a magnetostrictive or piezoelectric transducer for use in a dental scaler according to the invention.

According to the frequency variation of the current $i_w$ flowing through the coil 121 of transducer 104, driving the transducer 104 at the basic frequency $f_g$ causes a certain current in the transducer and hence generates a control signal U4 which is proportional to this current. An increase of the amplitude of this control signal causes an increasing opening of the transistor 124 and hence an increasing blocking of the transistor 125. As a result, the amplitude of the regulating voltage U6 appearing at the emitter of the transistor 125 is reduced. The oscillator, i.e. the multivibrator 102 is designed such that a reduction of the amplitude of the regulating voltage on the input terminal 118 leads to a reduction of the frequency. Therefore, according to FIG. 9, the current $i_w$ through the coil 121 of the transducer 104 increases still further and, owing to further increase in the amplitude of the control signal U4, leads to a further reduction of the amplitude, i.e. magnitude of the regulating voltage U6. This once again causes a further reduction of the oscillator frequency. The correction adjustment of the oscillator 102 occurs, in this case, starting from the basic frequency $f_g$, approximately along the curve N of FIG. 9, whereby this correction adjustment, and with it the regulating process, is terminated when the curve N once again intersects the current-frequency characteristic of the transducer 104 at a frequency below the basic frequency $f_g$. This is so because, in the case of a further reduction of the frequency of the oscillator 102 beyond this intersection point, the current through the transducer 104 will again be reduced or it will at least increase less than necessary, according to the curve N, for a further adjustment of the oscillator 102 towards lower frequencies. The variation of the curve N is established basically by the rate of amplification, i.e. the gain of transistors 124 and 125 and by the correction adjustment characteristics of the oscillator 102, as well as by the magnitude of resistance value of the resistors 129 and 130. The resistors, together with the input resistance of the oscillator 102 (resistor parallel to the input 113 of the oscillator 102), form a voltage divider. The area shown with crosshatched lines in FIG. 9 is established as the correction adjustment region. The curve N can be shifted parallel to itself by a change of resistance value of the resistor 130, as indicated in FIG. 9 by means of broken lines, whence a different correction adjustment or pull-in region is established.

So far it has been assumed that no pressure is exerted on the tool 106 held on, i.e. secured to, the transducer 104. If this tool 106 is now, for example, pressed against the tooth of a patient for removal of tartar deposited on the tooth, then a displacement of the resonant frequency occurs and hence also of the frequency-dependent current flow through the coil 121 of the transducer 104, as indicated in FIG. 9 by means of the curve $i_w'$ shown in broken lines. It is seen that together with an increased load upon the tool 106, the resonant frequency of the transducer 104 will be displaced finally so far that the curve N no longer intersects the current-frequency characteristic of the transducer 104. When this condition has been reached, the switching arrangement becomes unstable and the frequency of the oscillator 102 is shifted towards a value which lies well outside the resonant frequency of the transducer 104. As a result, no noticeable oscillation amplitudes occur on the tool 106 and hence the transducer is no longer able to produce power. The device can be restarted so that, after the removal of the load upon the tool 106, the supply voltage $U_B$, for example by the actuation of a foot switch, is for a brief moment switched off and subsequently switched on again.

By an adjustment of the resistor 130 the curve N can be displaced within certain limits parallel to itself and hence the contact pressure for the tool can be adjusted. At this contact pressure, the above-described interruption of the frequency correction adjustment of the oscillator 102, i.e. a complete mistuning of this oscillator will result.

Figure 10:
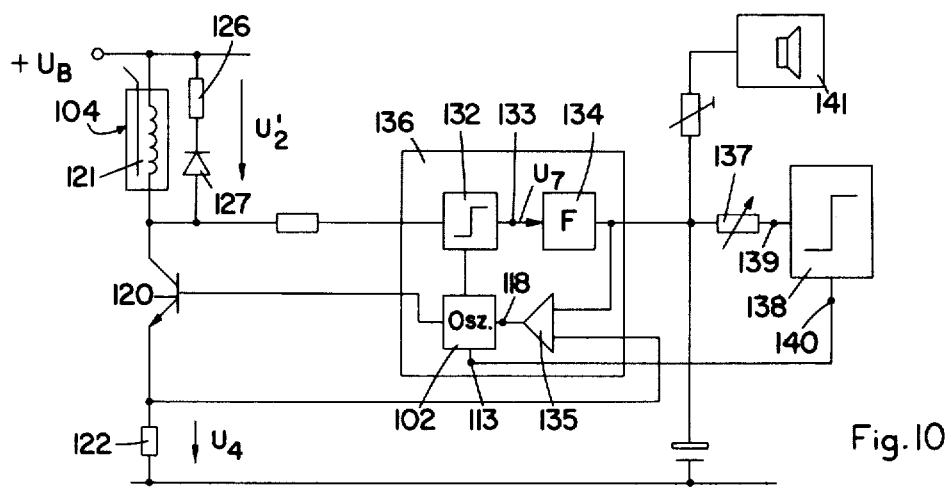
FIG. 10 is a modified embodiment of the control circuit of FIG. 7.

FIG. 10 shows a circuit in which the frequency-dependent phase variation of the voltage U2' in the coil 121 of the transducer 104, as well as the current-dependent compensating signal U4, are used for the correction adjustment of the oscillator 102. The circuit shown in FIG. 10 indicates for this purpose a phase comparison circuit 132, to which are supplied, on the one hand, a signal directly derived from the oscillator 102, and, on the other hand, a voltage U2' across the coil 121 of the transducer. Since the transducer 104 has oscillating circuit characteristics, the phase of the voltage U2' changes in relation to the frequency of the oscillator 102, so that a signal U7 is generated at the output terminal 133 of the phase comparison circuit 132, which is a measure of the adjustment of the oscillator 102 with reference to the resonant frequency of the transducer 104. This signal is supplied by the low pass filter 134 to one input of an amplifier 135 and it is transmitted, from the output of the amplifier 135, to the correction adjustment input 118 of the oscillator 102. The second input of the amplifier 135 receives the control signal U4 which is derived from the resistor 122 in the emitter circuit of transistor 120. As explained above, in conjunction with FIGS. 7 and 8, the amplitude of the control signal U4 depends on the frequency of the oscillator 102 and is used in the above-described manner for the correction adjustment of the oscillator 102. The control signal U4, as well as a signal U7 on the output 133 of the phase comparison circuit 132, are added in the amplifier 135 to form a combined signal used as the regulating voltage. These signals augment each other in the correction adjustment of the oscillator 102 in such a manner that, by means of control signal U4 or by means of the regulating voltage supplied by the control signal on the correction adjustment input 118, the oscillator 102 is brought into the vicinity of the instantaneous resonant frequency of the vibratory system of transducer 104, with the tool selected. Then, the fine adjustment of the oscillator 102 frequency is carried out by means of the signal U7 generated by the phase comparison circuit 132.

The phase comparison circuit 132, the low pass filter 134, the amplifier 135 as well as the oscillator, i.e. multivibrator 102, are a section of the embodiment shown in FIG. 10, as they constitute the fully integrated switching circuit 136, which is of the type known as a PLL (phase lock loop) switching circuit.

In order to ensure that the transducer 104 is switched off when a specific contact pressure of the tool 106 is exceeded, the signal U7 passes through the low pass filter 134 and is fed, via an adjustable resistor 137 which performs the function of the regulator 115 in the circuit of FIG. 7, to an amplifier circuit 138. This amplifier circuit 138, in the embodiment shown in FIG. 10, is designed so that a signal is generated at its output 140 only if the amplitude of the signal at the input 139 of the amplifier 138 has exceeded a specific threshold value. The amplifier 138 may be formed by a Schmitt trigger, for example.

The signal at the output 140 of the amplifier 138 is supplied to the input 113 of the oscillator 102 and is used preferably for adjusting the oscillator frequency. However, it is also possible, by means of the signal on the output 140 of the amplifier 138, to switch off the oscillator 102 or, as another alternative, to change its duty cycle.

The mode of operation of the switching off mechanism of the switching circuit shown in FIG. 10 is explained as follows. Each application of a load, i.e. each contact of the tool 106 with the tooth of a patient causes, according to the above explanation, a displacement of the mechanical resonant frequency of the vibratory system including the transducer 104. Then, a signal U7 is generated at the output 133 of the phase comparison circuit 132. This signal depends on this adjustment of the transducer 104 and hence constitutes a direct measure for the contact pressure of the tool 106. The higher the contact pressure of the tool 106, the higher will become the magnitude of the signal U7, or of that component of the signal U7 which is a function of displacement of the resonant frequency of the oscillator, as caused by a change in load. If the voltage U7 or the component of this voltage on the input 139 of the amplifier 138 supplied via the adjustable resistor 137, exceeds a specific threshold value, then a signal is generated at the output 140 of the amplifier 138. This signal adjusts the oscillator 102 to such an extent that it will be by far outside the resonant frequency of the transducer 104, so that the latter can no longer produce mechanical power. The magnitude of the signal U7 and hence the magnitude of the contact pressure of the tool 106, at which this switching off of the transducer 104 is carried out by a complete misadjustment of the oscillator 102, can be regulated by means of setting the variable resistor 137 to a corresponding resistance value according to the given requirements.

As shown also in FIG. 10, the output of the low pass filter 134 is also connected with a display device, which is formed, in the illustrated embodiment, by an acoustic signal source 141. This signal transducer is suitably adjusted by the dentist in such a manner that it will produce an acoustic signal shortly before the maximum permissible contact pressure of the tool 106 is reached, or shortly before the transducer 104 is switched off.

Figure 11:
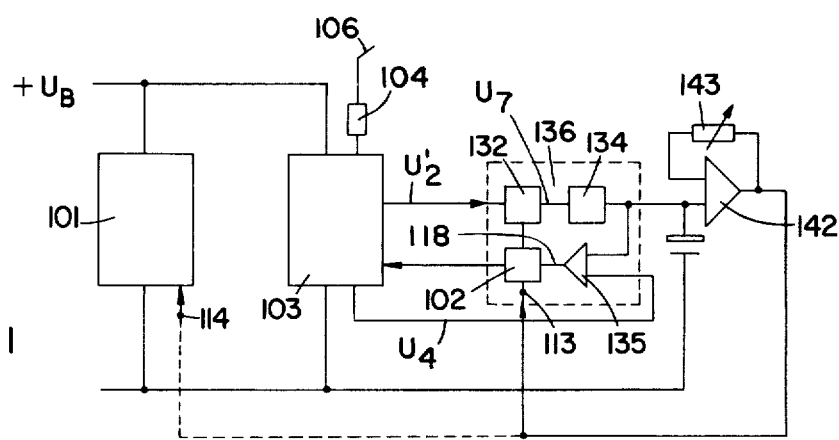
FIG. 11 is a second modified embodiment of the control circuit of FIG. 7.

FIG. 11 shows an embodiment which differs from the circuit shown in FIG. 10 basically by the fact that instead of an amplifier 138 which responds to a threshold value, an amplifier 142 is used, whose gain, i.e. amplification rate, can be continuously varied and which has switching characteristics. A variable resistor 143 is used for the adjustment of the rate of amplification. The amplifier 142 receives the signal U7 at the output of the low pass filter 134 and produces an output signal which can be supplied either to the input 113 of the oscillator 102 or else to the input 114 of the direct voltage supply source 101. The amplitude of signal on the output of the amplifier 142, in the same manner as the signal U7 amplitude on the output of the phase comparison circuit 132, is dependent upon the load applied to the tool 106 or on the contact pressure of this tool. This changes the frequency and/or the duty cycle of the oscillator 102 or the magnitude of the supply voltage $U_B$ in such a manner that the output power of the transducer 104 is reduced in proportion with the contact pressure of the tool 106. The extent of this power reduction can be adjusted by means of the resistor 143 in the feedback arm of the amplifier 142, so that, depending on the position of the variable resistor 143, a "softer or harder" power behavior of the transducer 104 or a greater or lower "hardness" for the transducer 104 can be arranged. In this manner it is ensured that the contact pressure of the tool 106 cannot exceed a specific, permissible maximum value.

An especially advantageous further embodiment of the invention has a LED (light-emitting diode) or digital figure display in an arrangement which indicates the adjusted maximum power, possibly in terms of adjusted, permissible contact pressure for the tool 106 and/or the releasing conditions of the safety circuit. In this case, it is useful to indicate the magnitudes related to the actual transducer conditions. The above, known as an absolute value display, is useful because the transducer 104 operates with different efficiency, depending upon the inserted tool 106 and upon the supply voltage $U_B$.

Especially advantageous in this case is a wobbling of the frequency regions by means of stored display of the theoretical permissible maximum power of the transducer 104 in comparison with an adjusted or preselected power output (regulator 115 or the resistors 130, 137 or 143) which is followed by the switching off of the transducer or by the reduction of the transducer power.

It should be noted that various modifications can be made to the circuits while still remaining within the purview of the following claims.

What is claimed is:

1. In a control circuit for an ultrasonic dental scaler including: a work tool; a transducer connected to said work tool for imparting vibratory motion thereto and forming a vibratory system therewith having a resonant frequency, said resonant frequency varying in response to variation of the contact pressure of said work tool against a tooth; an oscillator for driving said transducer; and said control circuit connected to said transducer and said oscillator for continuously readjusting the frequency of said oscillator to substantially the instantaneous resonant frequency of said vibrating system to thereby maintain substantially constant power output from said transducer, the improvement comprising:
   (a) sensing means connected to said control circuit for sensing a measured value indicative of the contact pressure of said work tool against said tooth; and
   (b) said sensing means being operative to reduce the output power of said transducer when a selected maximum contact pressure of said work tool against said tooth is exceeded by effecting in the frequency of said oscillator a change from said instantaneous resonant frequency.

2. A control circuit as set forth in claim 1 wherein the frequency of said oscillator is controlled by the level of a voltage applied to a frequency control input thereof, said transducer having a voltage thereacross during the driving thereof, said transducer voltage having a phase difference with respect to an output signal from said oscillator in proportion to the difference of the frequency of said oscillator from said instantaneous resonant frequency, said control circuit including:
   (a) phase comparison means having said transducer voltage and said oscillator output signal communicated thereto and having an output signal proportional to the phase difference of said transducer voltage and said oscillator output signal;
   (b) filter means receiving and filtering said signal proportional to said phase difference; and
   (c) means connecting said filter means to said oscillator frequency control input whereby the frequency of said oscillator is adjusted in response to the filtered signal to thereby tune said oscillator to said instantaneous resonant frequency.

3. In a control circuit for an ultrasonic dental scaler including: a work tool; a transducer connected to said work tool for imparting vibratory motion thereto and forming a vibratory system therewith having a resonant frequency, said resonant frequency varying in response to variation of the contact pressure of said work tool against a tooth; an oscillator for driving said transducer; and said control circuit connected to said transducer and said oscillator for continuously readjusting the frequency of said oscillator to substantially the instantaneous resonant frequency of said vibrating system to thereby maintain substantially constant power output from said transducer, the improvement comprising:
   (a) the frequency of said oscillator being controlled by the level of a voltage applied to a frequency control input thereof, said transducer having a voltage thereacross during the driving thereof, said transducer voltage having a phase difference with respect to an output signal from said oscillator in proportion to the difference of the frequency of said oscillator from said instantaneous resonant frequency;
   (b) phase comparison means having said transducer voltage and said oscillator output signal communicated thereto and having an output signal proportional to the phase difference of said transducer voltage and said oscillator output signal;
   (c) filter means receiving and filtering said signal proportional to said phase difference;
   (d) means connecting said filter means to said oscillator frequency control input whereby the frequency of said oscillator is adjusted in response to the filtered signal to thereby tune said oscillator to said instantaneous resonant frequency;
   (e) sensing means connected to said filter means of said control circuit and receiving said filtered signal for sensing a measured value indicative of the contact pressure of said work tool against said tooth; and
   (f) said sensing means being operative to reduce the output power of said transducer when a selected maximum contact pressure of said work tool against said tooth is exceeded by effecting a change in the frequency of said oscillator from said instantaneous resonant frequency whereby the output power of said transducer is reduced in response to a preselected level of said filtered signal.

4. A control circuit as set forth in claim 3 including: adjusting means connected to said sensing means and operable to vary the level of said filtered signal to which said sensing means is responsive to reduce said transducer output power.

5. A control circuit as set forth in claim 3 wherein: said sensing means is an amplifier the gain of which may be adjusted to set the level of said filtered signal to which said amplifier is responsive to reduce said transducer power output.

6. In a control circuit for an ultrasonic dental scaler including: a work tool; a transducer connected to said work tool for imparting vibratory motion thereto and forming a vibratory system therewith having a resonant frequency, said resonant frequency varying in response to variation of the contact pressure of said work tool against a tooth; an oscillator for driving said transducer; and said control circuit connected to said transducer and said oscillator for continuously readjusting the frequency of said oscillator to substantially the instantaneous resonant frequency of said vibrating system to thereby maintain substantially constant power output from said transducer, the improvement comprising:

(a) the frequency of said oscillator being controlled by the level of a voltage applied to a frequency control input thereof, said transducer having a voltage thereacross during the driving thereof, said transducer voltage having a phase difference with respect to an output signal from said oscillator in proportion to the difference of the frequency of said oscillator from said instantaneous resonant frequency;

(b) phase comparison means having said transducer voltage and said oscillator output signal communicated thereto and having an output signal proportional to the phase difference of said transducer voltage and said oscillator output signal;

(c) filter means receiving and filtering said signal proportional to said phase difference;

(d) means connecting said filter means to said oscillator frequency control input whereby the frequency of said oscillator is adjusted in response to the filtered signal to thereby tune said oscillator to said instantaneous resonant frequency;

(e) said means connected said filter means to said oscillator frequency control input being an amplifier having a pair of inputs, said filter means being connected to one of said inputs;

(f) current sensing means providing a signal proportional to the current flowing through said transducer during said driving thereof, said current being at a maximum when said vibratory system is operated at said instantaneous resonant frequency;

(g) said signal proportional to said current being applied to the other of said amplifier inputs whereby same is added with said filtered signal to thereby cooperatively adjust the frequency of said oscillator to said instantaneous resonant frequency;

(h) sensing means connected to said control circuit for sensing a measured value indicative of the contact pressure of said work tool against said tooth; and (i) said sensing means being operative to reduce the output power of said transducer when a selected maximum contact pressure of said work tool against said tooth is exceeded.

* * * * *